US007517647B2

(12) United States Patent
Rifkin et al.

(10) Patent No.: US 7,517,647 B2
(45) Date of Patent: Apr. 14, 2009

(54) GENETIC SCREEN FOR BIOACTIVE PEPTIDES

(75) Inventors: Daniel B. Rifkin, New York, NY (US); John S. Munger, New York, NY (US); Justin P. Annes, New York, NY (US)

(73) Assignee: New York University, New York, NY (US)

( * ) Notice: Subject to any disclaimer, the term of this patent is extended or adjusted under 35 U.S.C. 154(b) by 32 days.

(21) Appl. No.: 10/953,658

(22) Filed: Sep. 29, 2004

(65) Prior Publication Data

US 2005/0084844 A1 Apr. 21, 2005

Related U.S. Application Data

(60) Provisional application No. 60/506,973, filed on Sep. 29, 2003.

(51) Int. Cl.
*C12Q 1/68* (2006.01)
*C12Q 1/66* (2006.01)
*C12P 21/02* (2006.01)
*C12N 5/10* (2006.01)

(52) U.S. Cl. .............................. 435/6; 435/8; 435/69.1; 435/373

(58) Field of Classification Search ........................ None
See application file for complete search history.

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson et al. | |

OTHER PUBLICATIONS

Annes, J., et al., "A genetic screen to identify latent transforming growth factor beta activators", 2004, Analyt. Biochem., vol. 327: pp. 45-54.*
Abe, M., J. G. Harpel, C. N. Metz, I. Nunes, D. J. Loskutoff, D. B. Rifkin, An assay for transforming growth factor-beta using cells transfected with a plasminogen activator inhibitor-1 promoter-luciferase construct. *Anal. Biochem.* 216 (1994) 276-284.
Akhurst, R.J., R. Derynck, TGF-beta signaling in cancer—a double-edged sword. *Trends in Cell Biology.* 11 (2001) S44-51.
Annes, J. P., Rifkin, D. B., and Munger, J. S. (2002) *FEBS Lett.* 511, 65-68.
Annes, J. P., Munger, J. S., and Rifkin, D. B. (2003) *J. Cell Sci.* 116,217-224.
Ausubel et al., Current Protocols in Molecular Biology, John Wiley and Sons, Baltimore, Maryland (1989).
Birren et al (eds) Genome Analysis: A Laboratory Manual Series, vols. 1-4 Cold Spring Harbor Laboratory Press, New York (1998).
Blobe, G. C., Schiemann, W. P., and Lodish, H. F. (2000) *N. Engl. J. Med.* 342, 1350.

Chang, C., Z. Werb, The many faces of metalloproteases: cell growth, invasion, angiogenesis and metastasis. *Trends in Cell Biology.* 11 (2001) S37-43.
Chang, H., C. W. Brown, M. M. Matzuk, Genetic analysis of the mammalian transforming growth factor-beta superfamily. *Endocr. Rev.* 23 (2002) 787-823.
Cook, G., J. D. Campbell, C. E. Carr, K. S. Boyd, I. M. Franklin, Tranforming growth factor beta from multiple myeloma cells inhibits proliferation and IL-2 responsiveness in T Iymphocytes. *J. Leukoc. Biology.* 66 (1999) 981-988.
Cupp, A.S. Kim, G., and Skinner, M.K. (1999) *Biol. Reprod.* 60, 1304-1313.
Dabovic, B., Y. Chen, C. Colarossi, H. Obata, L. Zambuto, M. A. Perle, D. B. Rifkin, Bone abnormalities in latent TGF-beta binding protein (Ltbp)-3-null mice indicate a role for Ltbp-3 in modulating TGF-beta bioavailability. *J. Cell Biol.* 156 (2002) 227-232.
Dabovic, B., Y. Chen, C. Colarossi, L. Zambuto, H. Obata, D. B. Rifkin, Bone defects in latent TGF-b binding protein (Ltbp)-3 null mice; a role in TGF-b presentation. *J. Endocrinol.* 175 (2002) 129-141.
Dallas, S. L., K. Miyazono, T. M. Skerry, G. R. Mundy, L. F. Bonewal, Dual role for the latent transforming growth factor-beta binding protein in storage of latent TGF-beta in the extracellular matrix and as a structural matrix protein. *J. Cell Biol.* 131 (1995) 539-549.
Deng, H. K., Unutmaz, D., KewalRamani, V. N., and Littman, D. R. (1997) Nature 388, 296-300.
Dumont, N., C. L. Arteaga, The tumor microenvironment: a potential arbitrator of the tumor suppressive and promoting actions of TGFbeta. *Differentiation.* 70 (2002) 574-582.
Fernandez, T., Amoroso, S., Sharpe, S., Jones, G. M., Bliskovski, V., Kovalchuk, A., Wakefield, L. M., Kim, S. J., Potter, M., and Letterio, J. J. (2002) *J. Exp. Med.* 195, 1247-1255.
Gleizes, P.E., R. C. Beavis, R. Mazzieri, B. Shen, D. B. Rifkin, Identification and characterization of an eight-cysteine repeat of the latent transforming growth factor-beta binding protein-1 that mediates bonding to the latent transforming growth factor-beta 1. *J. Biol. Chem.* 271 (1996) 29891-29896.
Glick, A. B., Flanders, K. C., Danielpour, D., Yuspa, S. R., and Spom, M. B. (1989) *Cell Regul.* 1,87-97.

(Continued)

*Primary Examiner*—Michael Burkhart
(74) *Attorney, Agent, or Firm*—Kohn & Associates

(57) ABSTRACT

A method of screening for a protein involved in the extracellular regulation of latent TGFβ activation by transducing a cell line with a retroviral cDNA library to create a reporter cell line that produces green fluorescent protein (GFP) in response to TGF-β signaling; growing individual clones created by the reporter cell line; co-culturing each individual clone with a second TGF-β reporter cell line that produces luciferase in response to TGF-β, wherein the luciferase production identifies positive clones; and identifying a mechanism of latent TGF-β activation that is employed by the positive clones. A TGFβ reporter cell line including a cell line; and a retroviral cDNA library, wherein the reporter cell line produces GFP in response to TGF-β signaling. A method of screening for gene products involved in a biological process.

9 Claims, 3 Drawing Sheets

OTHER PUBLICATIONS

Harpel, J., S. Schultz-Cherry, J. E. Murphy-Ullrich, D. B. Rifkin, Tamoxifen and estrogen effects on TGF-b formation: role of thrombospondin-1, avb3, and integrin-associated proteins. *Biochem Biophys Res Commun.* 284 (2001) 11-14.

Hojo, M., T. Morimoto, M. Maluccio, T. Asano, K. Morimoto, M. Lagman, T. Shimbo, M. Suthanthiran, Cyclosporine induces cancer progression by a cell-autonomous mechanism. *Nature.* 397 (1999) 530-534.

Koli, K., J. Saharinen, M. Hyytiainen, C. Penttinen, J. Keski-Oja, Latency, activation, and binding proteins of TGF-beta. *Microsc. Res. Tech.* 52 (2001) 354-362.

Kulkarni, A.B., C. G. Huh, D. Becker, A. Geiser, M. Lyght, K. C. Flanders, A. B. Roberts, M. B. Sporn, J. M. Ward, S. Karlsson, Transforming growth factor beta 1 null mutation in mice causes excessive inflammatory response and early death. *Proceedings of the National Academy of Sciences USA.* 90 (1993) 770-774.

Li, J., H. Shen, K. L. Himmel, A. J. Dupuy, D. A. Largaespasa, J. D. Nakamura, J. Shaughnessy, N. A. Jenkins, N. G. Copeland, Leukaemia disease genes: large-scale cloning and pathway predictions. *Nat. Gent.* 23 (1999) 348-353.

Li, X., Zhao, X., Fang, Y., Jiang, X., Duong, T., Fan, C., Huang, C.C., and Kain, S.R. (1998) *J. Biol. Chem.* 273, 34970-34975.

Lund, A. H., Turner, G., Trubetskoy, A., Verhoeven, E., Wientjens, E., Hulsman, D., Russell, R., DePinho, R. A., Lenz, J., and van Lohuizen, M. (2002) *Nat. Genet.* 32, 160-165.

Lyons, R. M., Keski-Oja, J., and Moses, H. L. (1988) *J. Cell Biol.* 106, 1659-1665.

Massague, J., Blain, S. W., and La, R. S. (2000) *Cell* 103, 295-309.

Munger, J.S., J. G. Harpel, F. G. Giancotti, D. B. Rifkin, Interactions between growth factors and integrins: latent forms of transforming growth factor-b are ligands for the integrin avb1. *Mol. Biol. Cell.* 9 (1998) 2627-2638.

Mu, D., S. Cambier, L. Fjellbirkeland, J. L. Baron, J. S. Munger, H. Kawakatsu, D. Sheppard, V. C. Broaddus, S. L. Nishimura, The integrin alpha(v) beta8 mediates epithelial homeostasis through MT1-MMP-dependent activation of TGF-beta1. *J. Cell Biol.* 157 (2002) 493-507.

Nunes, I., P. E. Gleizes, C. N. Metz, D. B. Rifkin, Latent transforming growth factor-beta binding protein domains involved in activation and transglutaminase-dependent cross-linking of latent transforming growth factor-beta. *J. Cell Biol.* 136 (1997) 1151-1163.

Olofsson, A., K. Miyazono, T. Kanzaki, P. Colosetti, U. Engstrom, C. H. Heldin, Transforming growth factor-b 1, -b2, and -b3 secreted by a human glioblastoma cell line. Identification of small and different forms of large latent complexes. *J. Biol. Chem.* 267 (1992) 19482-19488.

PCR Protocols: A Guide To Methods And Applications, Academic Press, San Diego, CA (1990).

Perbal, A Practical Guide to Molecular Cloning, John Wiley & Sons, New York (1988).

Ramirez, F., L. Pereira, The fibrillins. *Int. J. Biochem. Cell Biol.* 31 (1999) 255-259.

Rayner, J.R., and Gonda, T.J. (1994) *Mol. Cell. Biol.* 14, 880-887.

Rodriguez, C., Huang, L. J., Son, J. K., McKee, A., Xiao, Z., and Lodish, H. F. (2001) *J. Biol. Chem.* 276, 30224-30230.

Sambrook et al., Molecular Cloning: A Laboratory Manual, Cold Spring Harbor Laboratory Press, New York (1989).

Sanford, L.P., I. Ormsby, A. C. Gittenberger-de Groot, H. Sariola, R. Friedman, G. P. Boivin, E. L. Cardelll, T. Doetschman, TGFbeta2 knockout mice have multiple developmental defects that are non-overlapping with other TGFbeta knockout phenotypes. *Development.* 124 (1997) 2659-2670.

Schultz-Cherry, S., H. Chen, D. F. Mosher, T. M. Misenheimer, H. C. Krutzsch, D. D. Roberts, J. E. Murphy-Ullrich, Regulation of transforming growth factor-beta activation by discrete sequences of thrombospondin 1. *J. Biol. Chem.* 270 (1995) 7304-7310.

Schultz-Cherry, S., J. Lawler, J. E. Murphy-Ullrich, The type 1 repeats of thrombospondin 1 activate latent transforming growth factor-b. *J Biol Chem.* 269 (1994) 26783-26788.

Schultz-Cherry, S., S. Ribeiro, L. Gentry, J. E. Murphy-Ullrich, Thrombospondin binds and activates the small and large forms of latent transforming growth factor-b in a chemically defined system. *J Biol Chem.* 269 (1994) 26775-26782.

Schultz-Cherry, S., and Murphy-Ullrich, J. E. (1993) *J. Cell. Biol.* 122; 923-932.

Shull, M.M., I. Ormsby, A. B. Kier, S. Pawlowski, R. J. Diebold, M. Yin, R. Allen, C. Sidman, G. Proetzel, D. Calvin, T. Doestchman, Targeted disruption of the mouse transforming growth factor-beta 1 gene results in multifocal inflammatory disease. *Nature.* 359 (1992) 693-699.

Sime, P. J., Z. Xing, F. L. Graham, K. G. Csaky, J. Gauldie, Adenovector-mediated gene transfer of active transforming growth factor- beta 1 induces prolonged severe fibrosis in rat lung. *J. Clin. Invest.* 100 (1997) 768-776.

Taipale, J., K. Miyazono, C. H. Heldin, J. Keski-Oja, Latent transforming growth factor-beta 1 associates to fibroblast extracellular matrix via latent TGF-beta binding protein. *J. Cell Biol.* 124 (1994) 171-181.

Testoni et al, 1996, Blood 87:3822.

Urashima, M., A. Ogata, D. Chauhan, M. Hatziyanni, M. B. Vidriales, D. A. Dedera, R. L. Schlossman, K. C. Anderson, Transforming growth factor-beta 1: differential effects on multiple myeloma versus normal B cells. *Blood.* 87 (1996) 1928-1038.

van Zoelen, E.J., van Oostwaard, T.M. and de Laat, S.W. (1986) *J. Biol. Chem.* 261, 5003-5009.

Watson et al., Recombinant DNA, Scientific American Books, New York.

Yu, Q., and Stamenkovic, I. (2000) *Genes Dev.* 14, 163-176.

Yehualaeshet, T., R. O'Connor, J. Green-Johnson, S. Mai, R. Silverstein, J. E. Murphy-Ullrich, N. Khalil, Activation of rat alveolar macrophage-derived latent transforming growth factor beta-1 by plasmin requires interaction with thrombospondin-1 and its cell surface receptor, CD36. *Am. J. Patholol.* 155 (1999) 841-851.

Anzano, M.A. et al. Synergistic interaction of two classes of transforming growth factors from murine sarcoma cells. (1982) *Cancer Res.* 42, 4776-4778.

Bonewald, L.F., L. Wakefield, R. O. Oreffo, A. Escobedo, D. R. Twardzik, Latent forms of transforming growth factor-beta (TGF beta) derived from bone cultures: identification of a naturally occurring 100-kDa complex with similarity to recombinant latent TGFbeta. Molecular Endocrinology. 5 (1991) 741-751.

Border, W.A., et al. Transforming growth factor-b in disease: the dark side of tissue repair. J. Clin. Invest. 90 (1992) 1-7.

Boulanger, J., et al. Mediation of Glucocorticoid Receptor Function by the Activation of Latent Transforming Growth Factor Beta 1 in MG-63 Human Osteosarcoma Cells (1995) Int. J. Cancer 61,692-697.

Crawford, S.E., et al. Thrombospondin-1 is a major activator of TGF-$\beta$1 in vivo . (1998) *Cell* 93, 1159-1170.

Harrington, J., et al. Creation of genome-wide protein expression libraries using random activation of gene expression (2001) Nat. Biotechnol. 19, 440-445.

Hocevar, B. A., et al. Isolation and characterization of mutant cell lines defective in transforming growth factor $\beta$ signaling. (1996) *Proc. Natl. Acad. Sci. USA* 93, 7655-7660.

Horimoto, M., et al. Identification of a transforming growth factor beta-1 activator derived from a human gastric cancer cell line. (1995) British J. Cancer 72,676-682.

Kaartinen, V., et al. Abnormal lung development and cleft palate in mice lacking TGF-$\beta$3 indicates defects of epithelial-mesenchymai interaction, (1995) Nat. Genet. 11, 415-421.

Knabbe, C., et al. Induction of Transforming Growth Factor $\beta$ by the Antiestrogens Droloxifene, Tamoxifen, and Toremifene in MCF-7 Cells, (1991) Am. J. Clin. Oncol. 14, S15-20.

Koli, K., et al. Vitamin $D_3$ and Calcipotriol Enhance the Secretion of Transforming Growth Factor-$\beta$1 and -$\beta$2 in Cultured Murine Keratinocytes (1993) Growth Factors 8, 153-163.

Miyazono, K., et al. Latent high molecular weight complex of transforming growth factor beta 1. Purification from human platelets and structural characterization. (1988) *J Biol Chem.* 263, 6407-15.

Miyazono, K., et al. A role of the latent TGF-b 1-binding protein in the assembly and secretion of TGF-b 1. (1991) *EMBO J.* 10, 1091-1101.

Munger, J.S., et al. Latent transforming growth factor-b: Structural features and mechanisms of activation. *Kidney International* vol. 51 (1997) pp. 1376-1382.

Munger, J.S., et al. The integrin αvβ6 binds and activates latent TGF-beta 1: A mechanisms for regulating pulmonary inflammation and fibrosis. (1999) *Cell*. 96, 319-328.

Murphy-Ullrich, J.E., et al. Activation of latent TGF-beta by thrombospondin-1: mechanisms and physiology. (2000) *Cytokine Growth Factor Rev*. 11, 59-69.

Onishi, M., et al., Applications of retrovirus-mediated expression cloning. Exp. Hematol. 24 (1996) 324-329.

Oursler, M. J., et al. Glucocorticoid-Induced Activation of Latent Transforming Growth Factor-β by Normal Human Osteoblast-Like Cells (1993) Endocrinology 133, 2187-2196.

Proetzel, G., et al. Transforming growth factor-beta 3 is required for secondary palate fusion. (1995) *Nature Genetics*. 11, 409-414.

Rifkin, D.B., R. Mazzieri, J. S. Munger, I. Noguera, J. Sung, Proteolytic control of growth factor availability. APMIS. 107 (1999) 80-85.

Saharinen, J., et al. Association of the small latent transforming growth factor-beta with an eight cysteine repeat of its binding protein LTBP-1. (1996) *EMBO J*. 15, 245-253.

Saharinen, J., et al. Latent transforming growth factor-beta binding proteins (LTBPs) structural extracellular matrix proteins for targeting TGF-beta action. (1999) *Cytokine Growth Factor Rev*. 10, 99-117.

Saharinen, J., et al. Specific sequence motif of 8-cyc repeats of TGF-beta binding proteins, LTBPs, creates a hydrophobic interaction surface for binding of small latent TGF-beta. (2000) *Mol. Biol. Cell*. 11, 2691-2704.

Simonsen, H., et al. (1994) Cloning by function: expression cloning in mammalian cells. Trends Pharmacal. Sci. 15, 437-441.

Stark, G. R., et al. Forward genetics in mammalian cells. (1999) *Hum. Mol. Genet*. 8, 1925-1938.

Sun, P., et al. p53-Independent role of MDM2 in TGFΟβ1 resistance (1998) *Science* 282, 2270-2272.

Taipale, J., et al. Extracellular Matrix Associated Transforming Growth Factor-b: Role in Cancer Cell Growth and Invasion (1998) Adv. Cancer Res. 75, 87-134.

Wang, R. F. et al. Developm,ent of a Retrovirus-based Cmplementary DNA Expression System of rhte Cloning of Tumor Antigens (1998) Cancer Res. 58,3519-3525.

Wrana, J.L., et al. TGF-beta signals through a heteromeric protein kinase receptor complex. (1992) *Cell*. 71, 1003-1014.

Zhong, Z., et al. Stat3: A STAT Family Member Activated by Tyrosine Phosphorylation in Response to Epidermal Growth Factor and Interleukin-6 (1994) Science 264, 95-98.

\* cited by examiner

SEQUENCE LISTING

<160> NUMBER OF SEQ ID NOS: 4

<210> SEQ ID NO 1
<211> LENGTH: 30
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(30)
<223> OTHER INFORMATION: PRIMER

<400> SEQUENCE: 1
caccgccctc aaagtagacg gcatcgcagc          30

<210> SEQ ID NO 2
<211> LENGTH: 23
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(23)
<223> OTHER INFORMATION: Primer

<400> SEQUENCE: 2
ctacaggtgg ggtctttcat tcc          23

<210> SEQ ID NO 3
<211> LENGTH: 24
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(24)
<223> OTHER INFORMATION: Primer

<400> SEQUENCE: 3
caccggacca tcctctagac tgcc          24

<210> SEQ ID NO 4
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(26)
<223> OTHER INFORMATION: Primer

<400> SEQUENCE: 4 ccttttctg gagactaaat aaaatc          26

GENETIC SCREEN FOR BIOACTIVE PEPTIDES

CROSS REFERENCE TO RELATED APPLICATIONS

This application claims the benefit of priority under 35 U.S.C. Section 119(e) of U.S. Provisional Patent Application No. 60/506,973, filed Sep. 29, 2003, which is incorporated herein by reference in its entirety.

BACKGROUND OF THE INVENTION

1. Technical Field

The present invention relates to recombinant DNA technology and more specifically towards genetic screens for identifying protein activities.

2. Background Art

The use of forward genetics has led to the identification of gene products involved in numerous processes from retroviral infection to signal transduction to oncogenesis (Deng, H. K., et al., Lund, A. H., et al., Walting, D., et al., and Zhong, Z., et al.). The power of these approaches rests in the virtual exclusion of experimenter bias and the breadth of candidate genes that can be tested in a single experiment. Every forward genetics technique, however, possesses intrinsic advantages and limitations (Stark, G. R., et al.). For instance, retrovirus-based insertional mutagenesis has the advantage of nearly random proviral insertion, which results in relatively normalized gene targeting. This allows one to reveal gain-of-function effects through gene activation even for rarely expressed or normally tissue-specific gene products. Because most eukaryotic cell lines are polyploid, however, repeated targeting of a single locus is required for loss-of-function effects (Harrington, J. J., et al.). By comparison, cDNA library-based expression cloning can uncover both gain-of-function and loss-of-function effects; although, it is often limited by unequal gene representation within the cDNA library (Simonsen, H., et al.). Because the strength of one experimental approach is often the defect of another, two experimental approaches can be combined towards a synergistic gain in screening power. For example, retrovirus-based insertional mutagenesis and cDNA expression cloning can be combined in a screen that aims to identify a specific protein activity.

Cytokines are a unique family of growth factors. Secreted primarily from leukocytes, cytokines stimulate both humoral and cellular immune responses, as well as the activation of phagocytic cells. One type of cytokine is the transforming growth factor βs (TGFβ). TGFβ was originally characterized as a protein (secreted from a tumor cell line) that was capable of inducing a transformed phenotype in non-neoplastic cells in culture. This effect was reversible, as demonstrated by the reversion of the cells to a normal phenotype following removal of the TGFβ. Subsequently, many proteins homologous to TGFβ have been identified. The four closest relatives are TGFβ1 (the original TGFβ) through TGFβ5 (TGFβ1 through TGFβ4). All four of these proteins share similar amino acid regions.

The TGFβ related family of proteins includes the activin and inhibin proteins. There are activin A, B, and AB proteins, as well as an inhibin A and inhibin B protein. The Mullerian inhibiting substance (MIS) is also a TGFβ related protein, as are members of the bone morphogenetic protein (BMP) family of bone growth-regulatory factors. Indeed, the TGFβ family can comprise as many as 100 distinct-proteins, all with at least one region of amino-acid sequence homology.

TGFβs have proliferative effects on many mesenchymal and epithelial cell types. Under certain conditions TGFβ demonstrates anti-proliferative effects on endothelial cells, macrophages, and T- and B-lymphocytes. Such effects include decreasing the secretion of immunoglobulin and suppressing hematopoiesis, myogenesis, adipogenesis, and adrenal steroidogenesis. Several members of the TGFβ family are potent inducers of mesodermal differentiation in early embryos, in particular TGF-β and activin A.

TGFβs, specifically TGFβ1, 2, and 3, are multipotent cytokines that are important modulators of cell growth, inflammation, matrix synthesis, the immune system, angiogenesis, and apoptosis (Taipale, J., et al.). Defects in TGFβ function are associated with a number of pathological states including immunosuppression, tumor cell growth, fibrosis, and autoimmune disease (Blobe, et al.). The TGF-βs are the prototypes of the TGF-β superfamily that consists of over 40 members that control key events in early development, patterning, tissue repair and wound healing. Although much is known about the regulation of TGF-β expression and signaling, the control of extracellular TGF-β availability is poorly understood. This is important because TGF-β is released as part of a latent complex in which the cytokine cannot interact with its receptor.

For TGF-β to signal, it must be released from its inactive complex by a process called activation. The latent complex consists of the 25 kD TGF-β homodimer, the TGF-β propeptides, also called the latency associated protein (LAP), and the latent TGF-β binding protein (LTBP). Even though the bond between the TGF-βs and LAP is cleaved within the Golgi, the TGF-β propeptide remains bound to TGF-β by non-covalent interactions. The complex of TGF-β and LAP is called the small latent complex (SLC). It is the association of LAP and TGF-β that confers latency. LAP-TGF-β binding is reversible and the isolated purified components can recombine to form an inactive SLC.

An important consideration for TGF-β action is the difference between the terms "activation" and "processing." For the TGF-βs, the term "processing" refers to the proteolytic cleavage of the bond between TGF-β and LAP. Without cleavage, no TGF-β activity can be detected in the precursor TGF-β dimer under any conditions. Cleavage is a prerequisite for activity. The term "activation" refers to the liberation of the TGF-β dimer from its interaction with LAP. Therefore, the "processed" TGF-β precursor has the potential to be activated, i.e. to release TGF-β, whereas the unprocessed TGF-β cannot be activated without initially cleaving (processing) the propeptide bond.

Several molecules have been described as latent TGF-β activators. The first cell-mediated activation process in which several cell types converted the LLC, which is produced constitutively by most cells, into active TGF-β by a protease-dependant reaction was by proteases. Latent TGF-β activation required a) the protease urokinase plasminogen activator (uPA), b) activation of uPA's substrate plasminogen (the zymogen of the protease plasmin), c) binding of LAP to cell surface mannose-6 (M6P) phosphate/IGF-II receptors, d) LTBP, and e) TGase, as antibodies and/or inhibitors of each of these reactants blocked latent TGF-β activation. A number of other proteases, including MMP-2, MMP-9, plasmin, calpain, chymase, and elastase have subsequently been described as latent TGF-β activators (Koli, et al. (2001)).

A second mechanism for latent TGF-β activation involves the interaction of the matricellular protein thrombospondin (TSP-1) with latent TGF-β in a multi-molecular complex containing TSP-1 receptors as well as CD36, and, in some cases, plasmin. Latent TGF-β activation involves a direct interaction between TSP-1 and LAP and includes the tripeptide sequence RFK found in the TSP-1 type 1 repeats. This peptide is believed to interact with the conserved tetra peptide LSKL in the LAP amino terminus disrupting the non-covalent association between LAP and TGF-β. A tetra peptide KRFK will activate latent TGF-β in vitro and in vivo, whereas addition of the LAP peptide (LSKL) in excess blocks latent TGF-β activation. TSP-1$^{-/-}$ mice show a partial, overlapping phenotype with TGF-β1$^{-/-}$ mice with respect to enhanced inflammation. The administration of the LSKL blocking peptide to wild type mice induces pancreas and lung pathologies similar to those observed in TGF-β$^{-/-}$ animals, whereas the addition of the KRFK activating peptide to TSP-1$^{-/-}$ mice reverts the phenotype towards normal. However, the phenotype of the TSP-1$^{-/-}$ mouse does not replicate the full phenotype of the TGF-β1$^{-/-}$ mouse nor does the TSP-1$^{-/-}$ phenotype resemble any of the phenotypes of the TGF-β2$^{-/-}$ or TGF-β3$^{-/-}$ mice. These discrepancies again suggest that there may be multiple and isoform specific mechanisms for activation of latent TGF-β.

Latent TGF-β can be activated by mild acid (pH 4.5), which probably destabilizes the interaction between LAP and TGF-β. However, except for specialized situations, such as the extracellular compartment formed by osteoclasts during bone resorption, this pH is probably rarely achieved in the extracellular environment in vivo. Therefore, pH is unlikely to be a common mechanism for TGF-β activation.

The TGF-β1 and β3, but not TGF-β2, propeptides contain the integrin recognition sequence RGD. TGF-β1 and TGF-β3 LAPs interact with cells expressing the integrins αvβ1 and αvβ5. Although the binding of latent TGF-β with these integrins does not result in activation, the ligation of latent TGF-β with αvβ6 results in activation (J. S. Munger, et al (1999)). Activation of latent TGF-β1 or β3 by αvβ6 requires the RGD sequence as mutant forms of TGF-β1 or β3 containing RGE fail to be activated. The integrin, αvβ8, in combination with MT1-MMP, activates latent TGF-β (D. Mu, et al, (2002)). The expression of integrin αvβ6 is restricted to epithelia, and under normal conditions β6 expression is low. However, during inflammation, β6 expression is enhanced dramatically (αv expression is constitutively high in most cells.) Because TGF-β is a powerful suppressor of inflammation, the heightened expression of β6, and subsequent activation of latent TGF-β, provides a potent mechanism for the down-modulation of the inflammatory state.

The ability of β6 integrin to activate latent TGF-β and the known profibrotic effects of TGF-β (W. A. Border, et al. (1992)) are illustrated in vivo by the fact that mice develop pulmonary inflammation followed by fibrosis in response to the inflammatory and profibrotic drug bleomycin. Because TGF-β enhances the expression of β6 by alveolar cells, bleomycin probably initiates a feed-forward mechanism by coordinately upregulating both integrin expression and TGF-β generation. In this scenario, fibrosis is the result of a failure to interrupt this loop. Interestingly, β6$^{-/-}$ mice have only a minor fibrotic response to bleomycin (J. S. Munger, et al. (1998)). However, although β6$^{-/-}$ mice display certain overlapping phenotypes with TGF-β1$^{-/-}$ mice, β6$^{-/-}$ mice do not phenocopy all aspects of TGF-β$^{-/-}$ mice. Moreover, there is no overlap of β6$^{-/-}$ and TGF-β3$^{-/-}$ phenotypes indicating that additional mechanisms exist for TGF-β3 generation.

Whereas the known mechanisms for latent TGF-β activation may account for the TGF-β observed in some situations, none of the established mechanisms accounts for all activation reactions; nor do these processes account for all of the TGF-β null phenotypes. Moreover, there are reports of active TGF-β production under conditions where the known mechanisms do not seem to apply. Certain glioblastoma or myeloma cell lines release active TGF-β, but this process cannot be blocked by inhibitors of TSP-1, proteases or αvβ6. These results indicate that activation mechanisms in addition to those already described exist.

An unusual property of TGFβ is that its activity is limited by the conversion of latent TGFβ to active TGFβ (a process termed latent TGFβ activation). Tissues contain significant quantities of latent TGFβ and activation of only a small fraction of this latent TGFβ generates maximal cellular responses (Annes, et al. (2003)). Latency is conferred by the non-covalent interaction of the TGFβ propeptide, also called the latency associated protein (LAP), with the mature cytokine after cleavage of the bond between TGFβ and LAP has occurred (Annes, et al.). Once active, TGFβ binds and brings together its high affinity serine/threonine kinase type I and type II receptors and initiates a signal transduction cascade (Massague, et al.). Although genetic screens have identified molecules involved in TGFβ signaling (Hocevar, B. A., et al., Rodriguez, C., et al., and Sun, P., et al.), no screen as of yet identifies genes involved in the process of latent TGFβ activation.

A number of gene products are considered to be latent TGF-β activators, including the integrins $\alpha_v\beta_6$ (Munger, J. S., et al. and Annes, J. P., et al. (2002)) and $\alpha_v\beta_8$ (Mu, D., et al.), plasmin (Lyons, R. M., et al.), thrombospondin-I (Yu, Q., et al.), matrix metalloproteinases (Yu, Q., et al.), and others (Annes, J. P., et al., (2003)). However, there is limited in vivo supporting evidence that these molecules are latent TGFβ activators. In fact, the phenotypes of mice with null mutations in TGFβ1, 2, and 3 genes can only be partially accounted for by the currently identified latent TGFβ activating molecules (Kulkarni, A. B., et al., Sanford, L. P., et al., and Kaartinen, V., et al.). Furthermore, TGFβ is generated by unknown mechanisms by: (1) certain cell lines (Fernandez, T., et al., Horimoto, M., et al., and Olofsson, A., et al.); (2) cells treated with various compounds (retinoids (Glick, A. B., et al.), antiestrogens (Knabbe, C., et al.), vitamin D3 (Koli, K., et al.), glucocorticoids (Oursler, M. J., et al., and Boulanger, J., et al.); and (3) disease states (Border, W. A., et al., and Blobe, G. C., et al.).

Accordingly, there is a need for a method and screen that focuses on identifying the extracellular regulation or activity of bioactive signaling molecules. More specifically, there is a need for identifying latent TGF-β activators and the mechanisms of extracellular regulation of TGF-β.

SUMMARY OF THE INVENTION

The present invention provides a method of screening for a protein involved in the extracellular regulation of latent TGFβ activation by transducing a cell line with a retroviral cDNA library to create a reporter cell line that produces green fluorescent protein (GFP) in response to TGF-β signaling, wherein the reporter cell line secretes endogenous latent TGF-β such that, upon acquisition of a latent TGF-β activator, GFP expression is induced; growing individual clones created by the reporter cell line; co-culturing each individual clone with a second TGF-β reporter cell line that produces luciferase in response to TGF-β, wherein the luciferase production identifies positive clones; and identifying a mechanism of latent TGF-β activation that is employed by the positive clones. Further, the present invention provides a TGFβ reporter cell line including a cell line; and a retroviral cDNA library, wherein the reporter cell line produces GFP in response to TGF-β signaling and said reporter cell line secretes endogenous latent TGF-β such that, upon acquisition of a latent TGF-β activator, GFP expression is induced. Finally, the present invention provides a method of screening for gene products involved in a biological process including the steps of conducting retroviral insertional mutagenesis with retroviral-based expression cloning; and identifying a resulting gene product occurring in an extracellular environment.

BRIEF DESCRIPTION OF THE DRAWINGS

Other advantages of the present invention will be readily appreciated, as the same becomes better understood by reference to the following detailed description when considered in connection with the accompanying drawings wherein.

DESCRIPTION OF THE INVENTION

Figure 1:
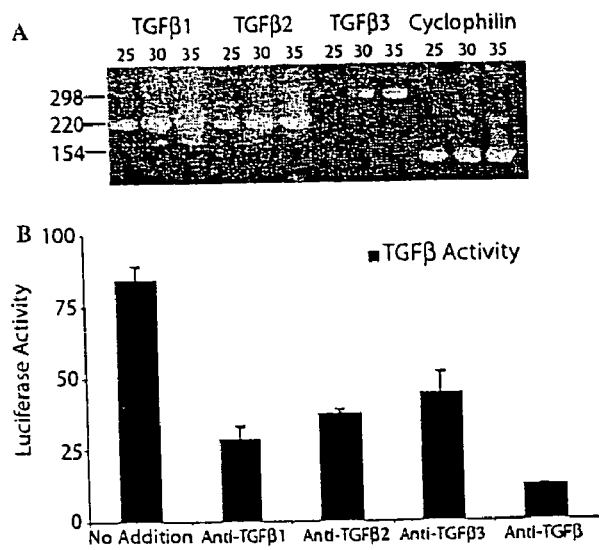
FIG. 1 is a diagram illustrating B9F cells producing and secreting TGFβ1, 2 and 3, wherein (A) RT-PCR was performed to determine the expression of TGFβ1, 2, and 3, and various numbers of PCR-cycles (25, 30 and 35) were used to qualitatively assess expression levels (experiment was repeated twice with similar results); (B) a TGFβ bioassay was performed using concentrated, heat-treated conditioned media generated by the B9F cell-line and isoform specific blocking antibodies were added as appropriate to cell cultures to determine the relative expression level of the various TGFβ isoforms, and all conditions were carried out in triplicate and the standard deviation of a single experiment is shown (experiment was repeated twice with similar results)

The present invention provides for a genetic screen, engineered cell line, and methods thereof for identifying proteins involved in the extracellular regulation of bioactive peptides. Specifically, the present invention utilizes retroviral mutagenesis and complementary DNA expression cloning to reveal proteins involved in the extracellular regulation of latent transforming growth factor β activation. More specifically, the present invention employs a cell line engineered to express green fluorescent protein (GFP) in response to transforming growth factor β (TGF-β).

The method of the present invention relies upon the generation of a reporter cell line that is engineered to produce GFP, or any other similar protein known to those of skill in the art, in response to bioactive peptide signaling. The reporter cell line secretes endogenous latent bioactive peptides such that, upon acquisition of a latent bioactive peptide activator, GFP expression is induced. The present invention can be used to identify individual activation mechanisms to TGF-β biology with respect to tumor biology. As a result, mechanisms for TGF-β formation in conditions relevant in both normal and pathological states can be determined and clarified. The present invention is useful in understanding the tumor phenotype as well as providing novel therapeutic targets.

The screen of the present invention for latent bioactive peptide activators is divided into two phases: an autocrine phase; and a paracrine phase. In the autocrine phase of screening, the reporter cell line is transduced with a retroviral cDNA library and enriched for GFP-bright cells by fluorescence activated cell sorting (hereinafter, "FACS"). After several rounds of FACS, the selected cells are sorted and grown as individual clones. In the paracrine screening phase, each clone is co-cultured with a second bioactive peptide reporter cell line that produces luciferase in response to the bioactive peptide (See, Abe, M., et al.). This co-culture is performed both in the presence and absence of a bioactive peptide inhibitor. Clones that induce luciferase expression in the absence of an anti-bioactive peptide antibody, but not in its presence, have the ability to activate the latent bioactive peptide. This second phase of screening excludes spurious GFP-bright cells and effectively focuses the screen upon the identification of molecular mechanisms that regulate intercellular communication. The last step of the method of the present invention is to identify the mechanism of the latent bioactive peptide activation that is employed by positive clones. This can be accomplished by (1) retrieval of the retrovirus' cDNA insert using polymerase chain reaction (hereinafter, "PCR") or, if necessary, (2) identification of the retrovirus integration site to identify potentially trans-activated gene products.

The present invention has numerous advantages over the prior art. In the prior art, genetic screens have been used productively to identify gene products involved in diverse processes (Stark, G. R., et al.). The present invention is advantageous over the prior art for at least two main reasons. First, by combining retroviral insertional mutagenesis with retroviral based expression cloning, gene products involved in a specific biological process (i.e., latent TGFβ activation) can be identified by multiple routes. For example, ectopic gene expression is achieved either by insertion based gene activation or by retrovirus-driven driven cDNA expression. Despite the fact that these two mechanisms of gene activation are intrinsic to the retrovirus-based cDNA expression cloning strategy, this fact is often not recognized or exploited (Rodriguez, C., et al., Sun, P., et al., Wang, R. F., et al., and Rayner, J. R., et al.). Second, the present invention focuses upon the regulation of molecules in the extracellular environment. This is achieved by sequentially employing autocrine and paracrine-based screening phases. In the autocrine phase of the screen of the present invention, cells that were isolated demonstrated enhanced GFP expression following retroviral transduction. Whereas some of the cells enriched on this basis had up-regulated GFP-expression as a result of increased TGFβ activity (~18%), most cells were GFP-bright due to other-mechanisms (e.g., impaired protein degradation leading to an increased GFP half-life). Thus, the induction of GFP expression was not a specific indicator for TGFβ activity. To minimize this background, TGFβ was measured in a paracrine-dependent assay. This phase of screening ensured that positive clones generate TGFβ that is active in the extracellular space. Therefore, the screen of the present invention effectively focuses upon the extracellular regulation of latent bioactive peptides such as, but not limited to, TGFβ.

Other advantages of the present invention over the prior art include, but are not limited to, a more rapid, sensitive, specific, and powerful screen. A reasonable anticipated time for conducting the screen is fifty days. This estimate is based upon the following time considerations: three days to synthesize a retroviral library (SuperScript Choice System for cDNA synthesis; Invitrogen), seven days to verify the library's composition and complexity by determining the number of independent bacterial colonies, the average insert size; and the presence of full length cDNA clones of genes that are expected to be contained within the library, three days to perform retrovirus infection of the reporter cell line, fourteen days to complete five rounds of FACS, nine days to expand individually sorted clones, three days to execute co-cultures with the TMLC reporter cell line to identify putatively positive clones, three days to verify positive clones and eight days to retrieve and identify the retrovirus inserts. Although additional time can be required to confirm that the identified cDNAs are responsible for the generation of TGFβ activity or to locate the site of retroviral integration using an inverse PCR strategy if a positional-effect of retrovirus integration is suspected, experiments with this screen have conformed to this time-line.

The screen of the present invention is both sensitive and specific because every clone that was identified as a putative positive or negative, during the paracrine phase of screening, retained that designation upon further testing. The data shown in Table 2 reveals that positive clones, which all express the $β_6$-integrin subunit, generate a luciferase activity that is 3-9 times the background luciferase activity of negative clones. Furthermore, the addition of a TGFβ inhibitor consistently reduces the luciferase activity to between ⅓ and ½ its value. The consistency of these results allows for the reliable identification of clones that have acquired the ability to activate latent TGFβ. Although it is possible that the $β_6$-integrin subunit is a superior latent TGFβ activator compared to those activators that remain to be identified, other known mechanisms of latent TGFβ activation (TSP-1 and MMPs) generate a similar relative luciferase response in the reporter TMLC reporter cell line used here (Yu, Q., et al., and Crawford, S. E., et al.). Therefore, the screen of the present invention can display similar sensitivity and specificity in identifying latent bioactive peptide activators.

The screen of the present invention is a powerful approach for the isolation of activators of latent bioactive peptides such as TGF-β. Each round of FACS allows for a twenty-fold enrichment of cells capable of activating TGFβ (at least 5% of the cells are background). Thus, over the course of five rounds, one can achieve a 32,000-fold enrichment. In practice, the background increases by roughly 8% each round and thus, the theoretical enrichment is closer to 7,000-fold over the course of five rounds of FACS. These numbers, however, are based upon screening an infinite number of cells with a 100% retention-rate of positive cells. In practice, a finite number of cells is screened, and it is likely that a positive cell only has approximately a 50% chance of falling within the region defined by the gate (See, FIG. 2B). These two factors decrease the power of the screen. However, the power of the screen is enhanced by a high multiplicity of infection. For instance, if each-reporter cell carries four retroviral inserts, on average the power of the screen is improved four-fold. Based upon the screen described above, where the frequency of a latent TGFβ activator began at frequency of 1:10,000 and finished at a frequency of approximately 1:5, 5 rounds of FACS yielded approximately a 2,000-fold enrichment. The strength of the screen is dramatically enhanced by the paracrine phase of screening in which greater than 2,000 clones can be individually tested. For instance, if a library containing a latent TGFβ activator with a frequency of 1:1,000,000 is introduced into the reporter cell line with a multiplicity of infection of four, 1 in 250,000 cells is capable of activating latent TGFβ. Thus, five rounds of FACS can enrich this cell to a frequency of 1 in 125 cells (2,000 fold enrichment). If 2,000 clones were tested in the paracrine phase of screening, one would anticipate identifying approximately sixteen positive clones. Therefore, the screen of the present invention can be used to identify latent TGFβ activators present in a retroviral library with a frequency of less than one in a million.

The present invention is useful in the academic study of extracellular regulation of signaling molecules. Additionally, the present invention can be used to identify latent bioactive peptide activation mechanisms and serve as a useful paradigm for research into the modulation of other signaling pathways. Moreover, the present invention can be used a diagnostic tool to identify and explore various diseases associated with bioactive peptides such as TGF-β, since such proteins are known to have a role in disease processes. In addition, the screen of the present invention can be used to study the extracellular regulation of other growth factors. For example, the present invention can be used to investigate the role of proteins that activate TNF-α, which is a cell-surface protein that undergoes a regulated activation step. Therefore, the present invention allows for the identification of molecules that regulate TNF-α shedding and allows a variety of other signaling cascades to be examined.

The present invention can also be used to screen various tumor cell lines for latent TGF-β activators. TGF-β has been implicated in the biology of a number of different tumors both in vivo and in vitro. The present invention allows for the identification of TGF-β activators in various normal and pathological states. Various cDNA libraries can be prepared from diseased tissue and screen the library as described herein.

The term "bioactive peptide" as used herein means, any protein having a latent and an active form that is regulated by a mechanism known to those of skill in the art. Examples of bioactive peptides include, but are not limited to, TNFα, TGFβ, myostatin, and any other similar bioactive peptides known to those of skill in the art.

In one embodiment of the present invention, there is provided a method of genetic screening to identify the mechanism by which latent TGFβ is converted to the active cytokine is determined. Specifically, a genetic screen that combines retroviral mutagenesis and cDNA expression cloning to reveal proteins involved in the extracellular regulation of latent TGFβ activation is used. The screen of the present invention employs a cell line engineered to express GFP in response to TGF-β. The cells produce their own latent TGF-β. Therefore, after transduction with a retroviral cDNA library that contains an insert for an activator of latent TGF-β, cells expressing the activator are GFP-bright. These cells are enriched by FACS and grown as individual clones. The isolated clones are co-cultured with a second TGF-β reporter cell line that produces luciferase in response to TGF-β. Cells that have acquired the ability to activate latent TGF-β induce luciferase expression in the absence but not in the presence of neutralizing antibodies to TGF-β. The activator expressed by the positive clones can be identified by retrieval of the retrovirus cDNA insert.

In another embodiment of the present invention, there is provide a reporter cell line that includes a cell line and a retroviral cDNA library, wherein the reporter cell line produces GFP in response to TGF-β signaling and said reporter cell line secretes endogenous latent TGF-β such that, upon acquisition of a latent TGF-β activator, GFP expression is induced. The cell line can be any cell including, but not limited to, kidney cells (NRK-49F), human pulmonary adenocarcinoma cells, multiple myeloma cells, gliomablastoma cells, primary cell strains, cells involved with GF-β action, and any other similar cell line known to those of skill in the art.

A further embodiment of the present invention provides a method of screening for gene products involved in a biological process by conducting retroviral insertional mutagenesis with retroviral-based expression cloning; and identifying a resulting gene product occurring in an extracellular environment. Identification of the resulting gene product is defined as sequentially employing autocrine and paracrine-based screening phases. Further, the autocrine-based screening phase includes determining enhanced GFP expression following retroviral transduction of the cells, while the paracrine-based screening phase includes determining that positive clones generate a gene product that is active in the extracellular environment.

The above discussion provides a factual basis for the use of the present invention. The methods used with a utility of the present invention can be shown by the following non-limiting examples and accompanying figures.

EXAMPLES

Materials and Methods:

Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds) *Genome Analysis: A Laboratory Manual Series, Vols.* 1-4 Cold Spring Harbor Laboratory Press, New York (1998) and methodology as set forth in U.S. Pat. Nos. 4,666,828; 4,683, 202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

Cell Lines and Reagents:

NRK-49F cells were obtained from American Type Culture Collection (Manassas, Va.). The TGFβ reporter mink lung cells were generated in our lab as previously described (Abe, M., et al.). All cells were cultured in DMEM containing 10% heat-inactivated FCS. Recombinant simian TGFβ1 LAP was produced and purified as described previously (Munger, J. S., et al.). All molecular biology enzymes were purchased from Roche Diagnostics Corporation (Indianapolis, Ind.). Chemical inhibitors used in cell culture experiments were obtained from Sigma-Aldrich (St. Louis, Mo.). Retroviral production was accomplished using the Pantropic Retroviral Expression System and following the manufacturer's instructions (Clontech; Palo Alto, Calif.). Monoclonal antibodies 1D11 against active TGFβ (all isoforms), anti-TGFβ1 polyclonal chicken Ig (AF-IOI-NA), anti-TGFβ2 polyclonal goat IgG (AB-112-NA), and anti-TGFβ3 polyclonal goat IgG (AB-244-NA) are from R&D Systems, Minneapolis, Minn.

Retroviral Library and Expression Vectors:

The PMX-$\beta_6$ integrin vector was constructed by isolating the Pme/digestion fragment of pHygrobeta6 (Annes, J. P., et al. (2002)) and cloning it into filled-in Eco RI digested PMX virus. The 3TP-GFP-reporter construct was made by transferring the 3TP response element of the 3TP-luciferase construct (Asp 718/Xho/digested) (provided by J. Massague; Memorial Sloan-Kettering, N.Y.)(Wrana, J. L., et al.) into the similarly digested promoterless pd2-EGFP vector (Clontech). The correct coding sequence of all constructs was confirmed by automated sequencing.

To retrieve retroviral inserts from library-infected clones, genomic DNA was extracted using Easy-DNA (Invitrogen, Carlsbad, Calif.) following the manufacturer's instructions. The retroviral inserts were amplified using a nested PCR strategy (PCR 1: 5' primer-caccgccctcaaagtagacggcatcgcagc/ 3' (SEQ ID NO. 1) primer-ctacaggtggggtctttcattcc (SEQ ID NO. 2); PCR 2: 5' primer-caccggaccatcctctagactgcc/3' (SEQ ID NO. 3) primer-cctttctggagactaaataaaatc (SEQ ID NO. 4)) in a total volume of 100 µl. Reaction 1 was carried out and purified with a GFX-column (Amersham Biosciences, Piscataway, N.J.). Two microliters of purified material from PCR reaction 1 were used for the second PCR reaction. These primers are compatible with the pcDNA3.1 Directional TOPO Expression Kit (Invitrogen) that allows directional cloning and expression of PCR products.

RT-PCR:

RT-PCR was performed to determine expression of TGFβ 1, 2 and 3 by the NRK49F cell line and the B9F reporter cell line. RNA was extracted using Trizol (Invitrogen) from an 80% confluent 10 cm dish of cells according to the manufacturer's protocol. cDNA was synthesized from 2 µg of RNA and a portion of this product was used for PCR amplification of TGFβ isoforms and cyclophilin. Rat specific primers were as previously described (Cupp, A. S., et al.). The annealing temperatures used were 59.7° C. for TGFβ 1 and 2, and 51.4° C. for TGFβ3 and cyclophilin.

TGFβ Bioassays:

TGFβ bioassays were performed at three points: first, to verify the TGFβ isoforms secreted by the NRK-49F and B9F cells; second, during the screen to identify latent TGFβ activating clones; and third, with clones or established cell lines. To determine the amounts of TGFβ isoforms secreted by the NRK-49F and B9F cells, $4.5 \times 10^5$ cells were plated in 1.5 ml of 0.2% FCS/DMEM in a 30 mm well overnight. The conditioned media was collected and concentrated 6-fold using a 10,000 pa Centric on filter. The concentrated media was heated to 80° C. for 10 minutes to activate the latent TGFβ and added (50 µl/well) to Mink lung epithelial cells ($2.5 \times 10^4$) containing a transgene consisting of a TGFβ responsive PAI-I promoter fused to luciferase cDNA (Abe, M., et al.) that were plated in the wells of a 96-well microtiter plate. To determine the isoform specific activity, no addition, isoform specific neutralizing antibodies or a pan-specific TGFβ neutralizing antibody (anti-TGFβ1 (1 µg/ml), anti-TGFβ2 (10 µg/ml), anti-TGFβ3 (25 µg/ml), IDII (25 µg/ml) were individually added to wells. At the concentrations used, slight cross-reactivity of the isoform specific antibodies occurs.

For the identification of latent TGFβ activating clones, individual clones were allowed to reach confluence in the wells of a 96-well microtiter plate. The clones were trypsinized and split equally among three 96-well microtiter plates (50 µl per well). Mink lung epithelial cells (TMLC) containing a transgene consisting of TGF-β responsive element of the PAI-I promoter fused to luciferase cDNA were used for the assay (Abe, M., et al.). The reporter TMLC ($2.5 \times 10^4$), suspended in DMEM/IO % FCS, was added to two of the test plates in an equal volume (50 µl per well). The third plate was kept as a master plate. To one of the 96-well plates, LAP was added to a final concentration of 10 µg/ml per well to inhibit TGFβ activity. The cells were incubated for 16 hours and cell lysates prepared and assayed for luciferase activity (Abe, M., et al.). To measure TGFβ activation by established clones or cell lines, the protocol was identical except the test cells were counted ($1.5 \times 10^4$/well in 50 µl) and suspended in DMEM/10% FCS prior to the addition of TMLC. The data presented for these co-culture experiments shows the mean and the standard error of the mean of a single experiment. Each experiment was repeated at least two times with similar results.

Flow Cytometry:

Cells were washed with PBS, and incubated with primary antibody for 20 minutes followed by phycoerythrin-conjugated secondary antibody (Roche) for 20 minutes at 4° C. Cells were resuspended in PBS and analyzed by FACScan (Becton Dickinson, Rutherford, N.J.). Cell sorting was carried out using a Coulter GPICS Elite machine (Beckman Coulter).

Results:

Production of a TGFβ Reporter Cell Line and Determination of a Sorting Protocol:

To establish a TGFβ reporter cell line, normal rat kidney cells (NRK49F) were transfected with a vector encoding a TGFβ response element (3TP) upstream of a green fluorescent protein (GFP) and subjected to neomycin selection. NRK49F cells were used because they are TGFβ responsive, demonstrate contact-dependent growth inhibition, which is not disrupted by TGFβ in the absence of EGF (van Zoelen, E. J., et al.), and are not growth inhibited by TGFβ (Anzano, M. A., et al.). These properties ensure reliable GFP induction upon TGFβ stimulation and allow for relatively large-scale experimentation by a few individuals. In addition, NRK 49F cells secrete latent TGFβ1, 2, and 3 as determined by RT-PCR and bioassay. The endogenous expression of these latent TGFβ isoforms is important as the screen relies upon the identification of a cell that acquires an autocrine TGFβ signaling loop (i.e., the ability to activate and respond to its own TGFβ). The neomycin-resistant transfected NRK population was subsequently cloned by limiting dilution and screened for colonies that showed a TGF-dependent shift in fluorescence. The clone selected, B9F cells, also secretes TGFβ1, 2, and 3 as determined by RT-PCR and bioassay (FIGS. 1A and 1B).

Figure 2:
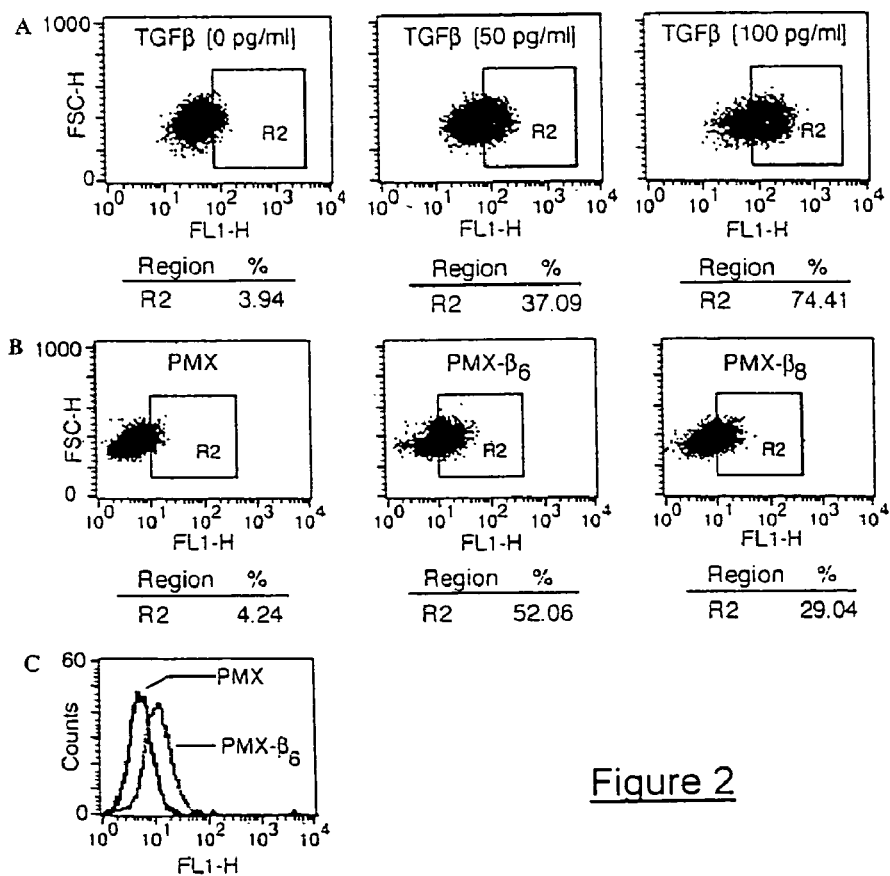
FIG. 2 illustrates the establishment and FACS characterization of a TGFβ reporter cell line and an NRK 49F-derived cell line (B9F) that expressed GFP in response to TGFβ was established, wherein (A) these cells were treated for sixteen hours with various concentrations of mature TGFβ (0, 50 and 100 pg/ml) prior to fluorescence analysis; (B) the B9F reporter cell-line was transduced with a retrovirus that directed the expression of either the $β_6$ integrin subunit, the $β_8$ integrin subunit, or was empty (72 hours post-infection, the fluorescence profile of the infected cell population was analyzed with a dot-plot, nearly 100% of the target cells were transduced with retroviruses); and (C) overlaid histogram analyses of GFP expression by reporter cells that were mock infected or $β_6$ integrin subunit-infected.

When treated with as little as 50 pg/ml of TGFβ. B9F cells demonstrate a significant increase in fluorescence (FIG. 2A, compare left and middle panel). Although the rightward shift appears small, analyses consistently revealed an 8-12 fold enrichment of TGFβ-treated cells (37%), compared to untreated cells (3.9%), within a gate set to include the brightest 3 to 6% of untreated cells. At 100 pg/ml TGFβ, 74% of the cells moved into the gated sector. Based upon the above results, the B9F cells demonstrated the fundamental properties of a useful reporter cell line: a reproducible, highly sensitive and apparently uniform rightward shift in fluorescence.

The success of the approach rests upon the capacity to discriminate, on the basis of fluorescence, between cells that gain the ability to activate latent TGFβ and those that do not. Therefore, B9F cells that express a latent TGFβ activator must be brighter than reporter cells that do not. To determine if cells that express an activator are in fact brighter, B9F cells were transduced with the empty virus (PMX)(FIG. 2B, left panel), the 136-integrin subunit containing retrovirus (middle panel) or the $\beta_6$-integrin subunit containing retrovirus (right panel). Both the $\beta_6$- and $\beta_8$-integrin subunits are known to activate latent TGFβ when paired with endogenously expressed $\alpha_v$-integrin subunit (Mu, D., et al., and Munger, J. S., et al.). A viral titer high enough to infect nearly 100% of the target reporter cells as determined by surface staining for the relevant integrin was used. The introduction of a latent TGFβ activator into the B9F cells caused a rightward shift in their fluorescence (FIG. 2B). The larger shift observed with the $\beta_6$-infected population (48%) compared with the $\beta_8$-infected population (~25%) is consistent with a previous determination of relative latent TGFβ activating abilities of the two integrins (Mu, D., et al.). The rightward shift in fluorescence of the PMX-$\beta_6$-infected cells, compared to the PMX-infected cells, is nearly uniform (See, FIG. 2C). This suggests that all of the B9F/PMX-$\beta_6$ cells responded to TGF-β as they displayed a distribution of fluorescence centered on a new mean.

An additional requirement of the screen is that the reporter cells demonstrate an increase in fluorescence in an autocrine manner. To distinguish between autocrine and paracrine signaling, PMX-transduced and PMX-$\beta_6$-transduced cells were mixed at a ratio of 99:1 and cultured for a week prior to FACS. In this sort, as with all the others discussed below, the brightest cells were isolated based upon a gate set to include the brightest 5% of the untreated B9F cells. 5.5% of the PMX-transduced cell population and 6.3% of the mixed 1% PMX-$\beta_6$/99% PMX-transduced cells were contained within this gate (See, Table 1). The fluorescence intensity of the sorted cells was subsequently examined at day four. At four days after sorting, 5.1% of the PMX-transduced cells and 23.8% of the 1% PMX-$\beta_6$/99% PMX-transduced cells were contained within the 5% gate set using untreated B9F cells.

The enrichment of GFP-bright cells from the 1% PMX-$\beta_6$/99% PMX-transduced population, but not the PMX-transduced cells suggests that fluorescence is a marker for cells that activate latent TGFβ. Indeed, by measuring latent TGFβ activation by the sorted 1% PMX-$\beta_6$/99% PMX-transduced cell population and the unsorted 1% PMX-$\beta_6$/99% PMX-transduced cells at four days post-sort, latent TGFβ activating cells were enriched. The ability to cull cells that activate latent TGFβ from a background of non-activating cells implies that the shift in fluorescence of the activating cells resulted from autocrine TGFβ signaling.

Another consideration in developing this screen was that latent TGFβ activated by one cell might enhance the fluorescence of neighboring cells that lack the ability to activate latent TGFβ (paracrine signaling or neighbor effect). To minimize this effect, cells were plated at low density following FACS (25,000 cells/10 cm dish). When 1% PMX-$β_6$/99% PMX-transduced cells were analyzed seven days post-FACS, there was a significant decrease in the enrichment of GFP bright cells from day four (23.8%) to day seven (8.7%) (Table 1). The failure to maintain a high proportion of GFP-bright cells results from a GFP-dependent growth disadvantage. An alternative explanation is based upon the neighbor effect and the fact that the half-life of the enhanced GFP is greater than twenty-four hours (Li, X., et al.). According to this explanation, some of the GFP-bright cells at day four were not autonomously bright; instead, at the time of sorting they were bright due to the neighbor effect. These cells (background cells) might remain bright over the course of the first four days, due to GFP perdurance, before becoming dim. Although this explanation may contribute to some of the signal decay seen between day four and day seven, a similar affect occurs, although to a lesser extent, in the PMX-transduced cell population (See, Table 1). However, because there was no enrichment of fluorescence in the sorted PMX-infected cells, the loss of fluorescence from day four to day seven is due to the deleterious effects of GFP. However, to limit the neighbor effect and the GFP-induced growth disadvantage, reporter cells were kept at low cell density and sorted every three to four days when performing the screen.

Figure 3:
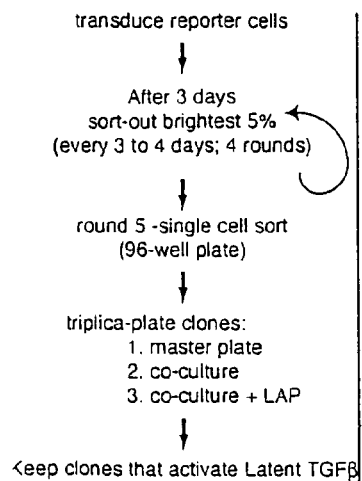
FIG. 3 illustrates a cell sorting protocol, wherein the B9F reporter cell line is transduced with a retroviral library on day 0, the infected cells are allowed three days to expand prior to cell sorting (doubling time=36 hours), a collection gate is set at the time of sorting to include the 5% brightest cells of a non-transduced B9F population that is grown in parallel (this gate is applied to the transduced reporter cells, which are sorted en masse and the sorting procedure is repeated three times with three to four day intervals), at the fifth round of sorting, cells that fall into the collection gate are individually sorted into the wells of a 96-well plate, these clones are expanded prior to triplicate plating, one of the three plates is used to maintain the clone, whereas the other two plates (plus and minus recombinant LAP (10 mg/ml) are used in a sixteen hour co-culture with a TGF-β reporter cell line that produces luciferase in response to TGF-β, and clones that generate a TGFβ activity of twice background are considered positive and are subjected to further testing.

Validation of Genetic Screen:

After establishing the reporter cell line, the genetic screen protocol was validated by determining if a known latent TFGβ activator (the $β_6$-integrin subunit) could be recovered from a complex retroviral library. To perform this experiment, the reporter cell line (≈500,000 cells) was transduced either with empty PMX virus or with virus generated from a thymic retroviral library that contained the PMX-$β_6$ viral DNA introduced at a ratio of 1:10,000. Target cells were plated at 50,000 cells per well in 10 cm tissue culture dishes. To maximize the number of screened retroviral inserts, the target cells were super-infected with an average of four infections per cell. The screening protocol that was used is outlined in FIG. 3. Three days post-infection, the infected reporter cells (PMX infected and PMX-library/$β_6$ infected) were subjected to FACS (≅1.0× $10^6$ cells from each population). The collection gate was set to include the brightest 5% of non-transduced reporter cells as described above. The sorted PMX and PMX-library/$β_6$ infected cells that fell within the collection gate were plated at low density (25,000 cells/10 cm dish) and allowed to recover for three to four days before sorting was repeated. In addition, at the time of the initial sort, a small proportion of the PMX and PMX-Library/$β_6$ infected cells were analyzed for $β_6$-integrin expression (FIG. 4A).

A cell line known to express the 136-integrin subunit was used as a positive control for the staining procedure. This analysis revealed no apparent difference between the two infected reporter cell populations; however, the control cell line showed strong 136-subunit staining. Therefore, the cells expressing the $β_6$-integrin were not a significant or identifiable population of the infected reporter cells at this initial time point.

Figure 4:
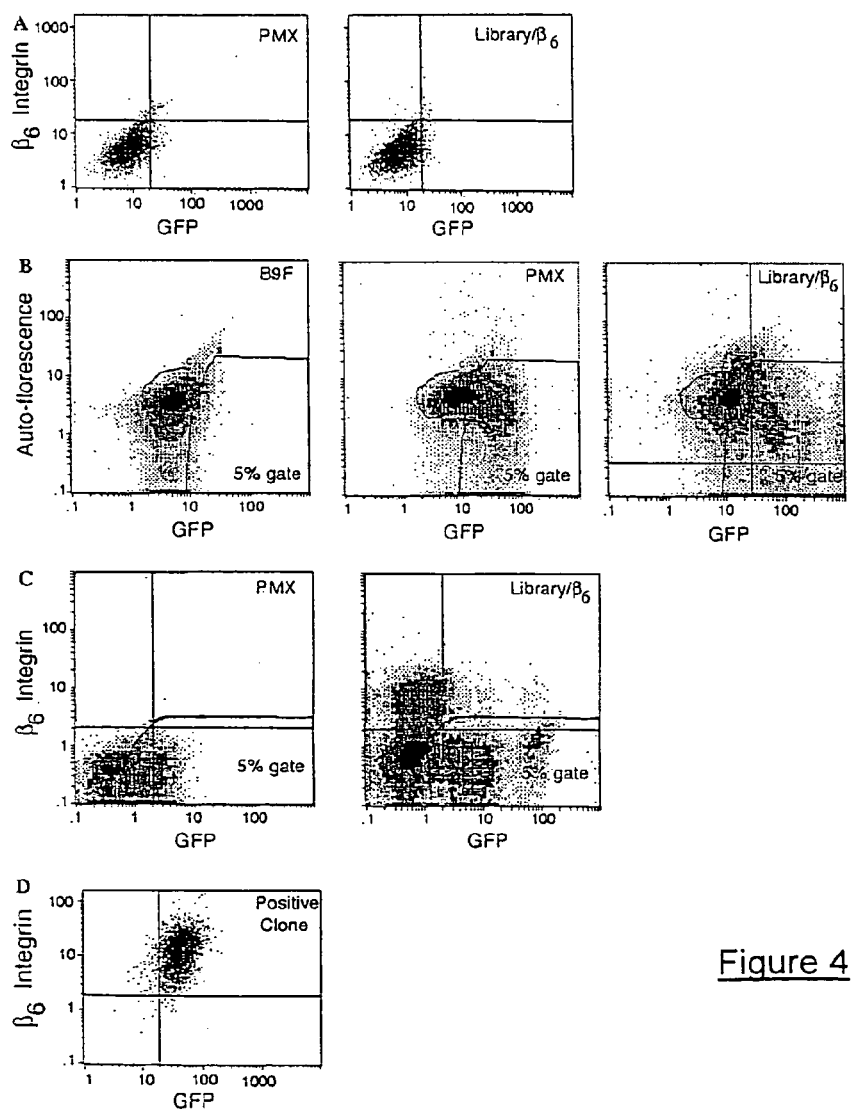
FIG. 4 illustrates the isolation by FACS of the $β_6$-integrin from a complex retroviral library, wherein a mixture of retroviral vectors containing a mouse thymus cDNA library and the $β_6$-subunit was made by mixing the pre-packaged retroviral, a cDNA library with the PMX-$β_6$ integrin retroviral vector at a ratio of 10,000 to 1 is produced where (A) B9F cells were transduced with empty PMX virus (left panel) or PMX virus that contained a mouse thymus cDNA library and the $β_6$-integrin (right panel)(three days after infection, a fraction of PMX-infected and library/$β_6$-infected cells were analyzed for $β_6$-integrin expression and GFP expression by fluorescence analysis), (B) the two populations of infected B9F cells shown in (A) were subjected to four rounds of sorting and these dot-plots are representative of the cell populations at the time of the fifth sorting round (the left panel shows the uninfected B9F cells used to set the collection gate, the center panel represents the PMX-infected cells and the right panel represents the library/$β_6$ infected cells, wherein the cells that fell within the collection gate in the center and right panel were individually sorted into the wells of a well plate), (C) a portion of the PMX-infected cells (left panel) and the library/$β_6$-infected cells (right panel) were analyzed for $β_6$-integrin expression by surface staining for $α_vβ6$ (representative dot-plot analyses of $α_vβ_6$ expression and GFP fluorescence are shown), (D) a typical clone that demonstrated $α_vβ_6$-dependent latent TGFβ activation in co-culture experiments was stained for $α_vβ_6$ surface expression and analyzed (compare to (A))

After four successive rounds of FACS, the fluorescence of both the PMX and the PMX-library/$β_6$ infected cells had changed substantially (FIG. 4B). At this point, FACS no longer had the potential to enrich activating clones as nearly half of the cell population was contained within the collection gate. Therefore, for the fifth FACS round, cells were individually sorted into wells of a 96-well plate. Approximately 2000 clones in the GFP-bright gate were collected (FIG. 4B) from both the PMX infected and the PMX-library/$β_6$ infected populations. In addition, we analyzed the $β_6$-integrin expression profile of a small proportion populations isolated by sequential FACS (FIG. 4C). Approximately 20% of the PMX-library/$β_6$-infected cells expressed the $β_6$-integrin subunit (FIG. 4C, right panel), whereas no expression was observed in PMX-infected cells (FIG. 4C, left panel). Therefore, the four rounds of FACS had effectively enriched the $β_6$-integrin subunit expressing cell population.

The ability of individual clones to activate latent TGFβ was assessed in co-cultures with TMLC both in the absence and presence of a TGFβ inhibitor (Annes, J. P., et al. (2002) and Abe, M., et al.). This was accomplished by triplicate plating the sorted clones to generate a master plate for preservation of the clones and two test plates (+/−TGFβ inhibitor, LAP). TMLCs were added to the test plates and the cells were incubated for sixteen hours before TGFβ generation was assessed. By using a co-culture to measure TGFβ generation by the cloned cells, we were able to distinguish between false positive cells (clones that were GFP-bright independent of TGFβ) and true positives (clones that generated active TGFβ).

Clonal growth occurred in approximately 75% of the wells into which single cells were sorted. Of these clones, approximately 18% of the PMX-library/$β_6$ sorted cell clones were considered to activate latent TGFβ, whereas 0% of the PMX sorted cells generated active TGFβ. The raw data from a typical 96-well microtiter plate are shown in Table 2. From this plate, growth of clones was evident in 79 of 96 wells. From these wells, eleven clones were considered to be positives. The criteria used in determining a clone to be positive were a significant induction of luciferase activity in the absence of a TGFβ inhibitor (>3,500 light units) and a greater than 2-fold difference in luciferase activity in the absence of a TGFβ inhibitor compared to its presence. Thus, the frequency with which clones were identified in the paracrine phase of screening accurately reflected the frequency of $β_6$-integrin positive cells at the fifth round of sorting (FIG. 4C).

Figure 5:
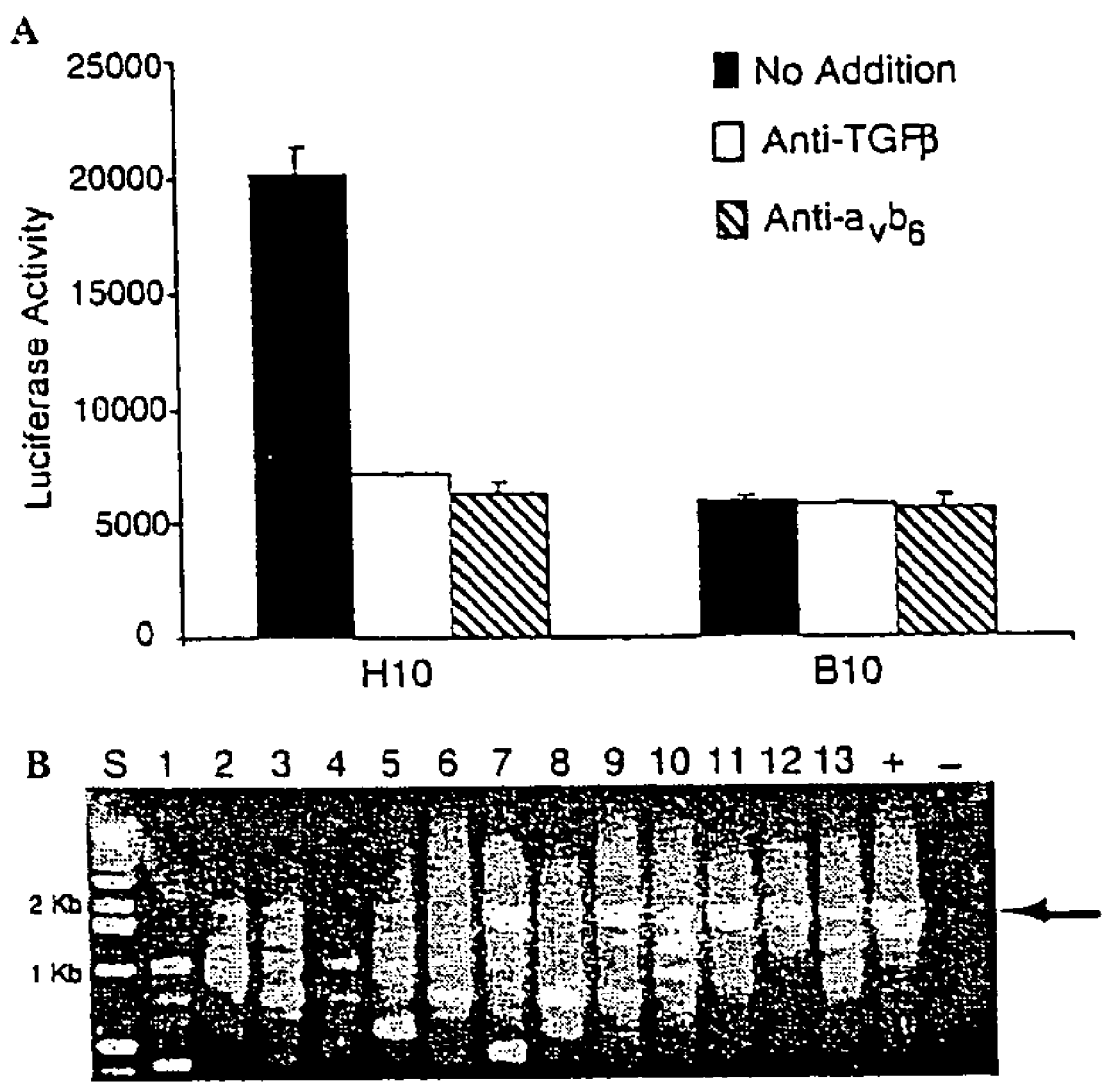
FIG. 5 illustrates a co-culture and PCR analysis of positive clones, wherein (A) putative positive (H 10) and negative (B 10) clones (Table 2) were retested for the ability to activate latent TGFβ in a co-culture assay with TGFβ reporter cells (TMLC) that produce luciferase in response to TGFβ (in order to determine the specificity of the luciferase activity, co-culture conditions were conducted in triplicate and included no addition, a TGFβ inhibitory antibody or an $α_vβ_6$-blocking antibody, wherein the average luciferase activity and the standard deviation of each co-culture condition are shown and this experiment was repeated twice with similar results), (B) genomic DNA was extracted from positive (lanes 2, 3, 5, 6, 7, 8, 9, 10, 11, 12, 13) and negative clones (lanes 1,4) that were identified as described above, wherein the genomic DNA from each clone was used as a template for nested PCR reactions to retrieve the retroviral inserts and the PCR reaction in the + lane used 25 ng of the PMX-$β_6$ retrovirus vector and the "−" lane contained no DNA template (the arrow indicates the expected size of the amplified band from the PMX-$β_6$ retrovirus DNA).

Once positive clones were identified, the next steps were to expand the clones, to re-test the cells for latent TGFβ activation in a co-culture assay, to determine if latent TGFβ activation was $α_vβ_6$-dependent, and to retrieve the retroviral inserts from positive clones. Typically, retested clones confirmed the results obtained in the previous round of screening. The results of a co-culture assay with two clones (B3 and HIO) from the representative plate shown in Table 2 are shown (FIG. 5A). Consistent with prior results, HIO cells were capable of activating latent TGFβ, whereas B3 cells were not. Latent TGFβ activation by the RIO cells was abrogated by an $α_vβ_6$-integrin blocking antibody. All positive clones that were identified by our screen activated latent TGFβ in an $α_vβ_6$-integrin dependent fashion. PCR-based retrieval of the retrovirus inserts from positive clones, but not negative clones, identified a band that co-migrated with the PCR product obtained using the PMX-$β_6$ retrovirus DNA as the template (FIG. 5B). Finally, fluorescence analysis of RIO cells (a positive clone) labeled with an anti-$β_6$-integrin antibody is shown in FIG. 4D. This clone is both $α_vβ_6$ and GFP bright (compare to FIG. 4A). Therefore, the screen of the present invention effectively enriched for and identified clones that activate latent TGFβ.

TABLE 1

Determination of the sorting frequency
Two populations of B9F cells, empty PMX-virus infected cells and 1% PMX-$\beta_6$/99% PMX-virus infected cells were sorted using a collection gate set based upon uninfected B9F cells. At the time of sorting, this gate included the brightest 5% of the B9F cells. The percentage of empty PMX-virus infected cells and 1% PMX-$\beta_6$/ 99% PMX-virus infected cells at the time of sorting, four days after sorting and sevendays after sorting are shown.

|  | Pre-sort | 4 days post-sort | 7 days post-sort |
|---|---|---|---|
| PMX | 5.5% | 5.1% | 5.3% |
| 99 PMX:1 PMX-$\beta_6$ | 6.3% | 23.8% | 8.7% |

TABLE 2

Typical results from the paracrine screening step.
GFP-bright clones were individually sorted into the wells of 96-well plates, expanded and plated in triplicate. One of the 96-well plates was kept as a master plate and the other two were used for coculture assays with TGFβ reporter cells (TMLCs) that produce luciferase in response to TGFβ. The co-culture assays were performed either in the absence or presence of a TGFβ inhibitor (LAP, 5 ng/ml). The results obtained from a typical 96-well plate of clones are shown.

No Addition:

| 2823 | 13681 | 2116 | 3365 | 2772 | 2263 | 2107 | 3601 | 1952 | 2159 | 2028 | 1476 |
|---|---|---|---|---|---|---|---|---|---|---|---|
| 1954 | 1878 | 6827 | 2563 | 2220 | 2251 | 2430 | 1857 | 1988 | 3431 | 2752 | 1449 |
| 1927 | 2828 | 2024 | 1327 | 13992 | 1716 | 1640 | 1859 | 1289 | 2160 | 1973 | 1894 |
| 4010 | 1426 | 7249 | 1617 | 2203 | 1250 | 1187 | 1865 | 1544 | 1664 | 1452 | 1597 |
| 3210 | 1530 | 3233 | 1645 | 4656 | 1236 | 3867 | 3115 | 3081 | 1708 | 3525 | 1687 |
| 2818 | 2524 | 2860 | 2842 | 1452 | 8911 | 1686 | 754 | 2763 | 3827 | 3549 | 1672 |
| 3643 | 2661 | 1274 | 2092 | 1315 | 1375 | 7027 | 1898 | 1353 | 1128 | 1486 | 2676 |
| 2116 | 2311 | 8358 | 12138 | 2835 | 1181 | 8826 | 17617 | 1514 | 6205 | 2367 | 1233 |

TGFβ inhibition:

| 2229 | 5509 | 3037 | 4098 | 2590 | 1509 | 2471 | 2728 | 2911 | 1536 | 2184 | 2916 |
|---|---|---|---|---|---|---|---|---|---|---|---|
| 2908 | 2342 | 3033 | 2034 | 1751 | 1872 | 2117 | 1924 | 2392 | 3642 | 2781 | 1795 |
| 2222 | 2413 | 1866 | 1712 | 5926 | 2036 | 2375 | 1949 | 1807 | 2021 | 1825 | 1893 |
| 3019 | 1742 | 3758 | 2090 | 2165 | 1613 | 1345 | 1629 | 2539 | 1962 | 1703 | 1571 |
| 2703 | 1778 | 2204 | 2100 | 3338 | 1464 | 4432 | 3046 | 2510 | 2160 | 2649 | 1945 |
| 2197 | 1667 | 3014 | 1964 | 1624 | 3858 | 1264 | 2493 | 3983 | 3210 | 3044 | 1866 |
| 3041 | 2167 | 1915 | 1844 | 2245 | 1180 | 2776 | 1652 | 1716 | 1696 | 2090 | 3170 |
| 1985 | 1514 | 3649 | 4968 | 3011 | 1351 | 3538 | 5718 | 1881 | 2053 | 2403 | 1655 |

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used, is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

REFERENCES

Abe, M., J. G. Harpel, C. N. Metz, I. Nunes, D. J. Loskutoff, D. B. Rifkin, An assay for transforming growth factor-beta using cells transfected with a plasminogen activator inhibitor-1 promoter-luciferase construct. *Anal. Biochem.* 216 (1994) 276-284.

Akhurst, R. J., R. Derynck, TGF-beta signaling in cancer—a double-edged sword. *Trends in Cell Biology.* 11 (2001) S44-51.

Annes, J. P., Rifkin, D. B., and Munger, J. S. (2002) *FEBS Lett.* 511, 65-68.

Annes, J. P., Munger, J. S., and Rifkin, D. B. (2003) *J. Cell Sci.* 116, 217-224.

Anzano, M. A. Roberts, A. B., Meyers, C. A., Komoriya, A., Lamb, L. C., Smith, J. M., and Sporn, M. B. (1982) *Cancer Res.* 42, 4776-4778.

Blobe, G. C., Schiemann, W. P., and Lodish, H. F. (2000) *N. Engl. J. Med.* 342, 1350-

Bonewald, L. F., L. Wakefield, R. O. Oreffo, A. Escobedo, D. R. Twardzik, Latent forms of transforming growth factor-beta (TGF beta) derived from bone cultures: identification of a naturally occurring 100-kDa complex with similarity to recombinant latent TGFbeta. *Molecular Endocrinology.* 5 (1991) 741-751.

Border, W. A., E. Ruoslahti, Transforming growth factor-b in disease: the dark side of tissue repair. *J. Clin. Invest* 90 (1992) 1-7.

Boulanger, J., Reyes-Moreno, C., and Koutsilieris, M. (1995) *Int J. Cancer* 61, 692-697.

Chang, C., Z. Werb, The many faces of metalloproteases: cell growth, invasion, angiogenesis and metastasis. *Trends in Cell Biology.* 11 (2001) S37-43.

Chang, H., C. W. Brown, M. M. Matzuk, Genetic analysis of the mammalian transforming growth factor-beta superfamily. *Endocr. Rev.* 23 (2002) 787-823.

Cook, G., J. D. Campbell, C. E. Carr, K. S. Boyd, I. M. Franklin, Transforming growth factor beta from multiple myeloma cells inhibits proliferation and IL-2 responsiveness in T lymphocytes. *J. Leukoc. Biology.* 66 (1999) 981-988.

Crawford, S. E., Stellmach, V., Murphy-Ullrich, J. E., Ribeiro, S. M., Lawler, J., Hynes, R. O., Boivin, G. P., and Bouck, N. (1998) *Cell* 93, 1159-1170. Sanford, L. P., Onnsby, I., Gittenberger-de Groot, A. C., Sariola, H., Friedman, R., Boivin, G. P., Cardell, E. L., and Doetschman, T. (1997) *Development* 124, 2659-2670.

Crawford, S. E., V. Stellmach, J. E. Murphy-Ullrich, S. M. Ribeiro, J. Lawler, R. O. Hynes, G. P. Boivin, N. Bouck, Thrombospondin-1 is a major activator of TGF-b1 in vitro. *Cell.* 93 (1998) 1159-1170.

Cupp, A. S. Kim, G., and Skinner, M. K. (1999) *Biol. Reprod.* 60, 1304-1313.

Deng, H. K., Unutmaz, D., KewalRamani, V. N., and Littman, D. R. (1997) *Nature* 388, 296-300.

Dabovic, B., Y. Chen, C. Colarossi, H. Obata, L. Zambuto, M. A. Perle, D. B. Rifkin, Bone abnormalities in latent TGF-beta binding protein (Ltbp)-3-null mice indicate a role for Ltbp-3 in modulating TGF-beta bioavailability. *J. Cell Biol.* 156 (2002) 227-232.

Dabovic, B., Y. Chen, C. Colarossi, L. Zambuto, H. Obata, D. B. Rifkin, Bone defects in latent TGF-b binding protein (Ltbp)-3 null mice; a role in TGF-b presentation. *J. Endocrinol.* 175 (2002) 129-141.

Dallas, S. L., K. Miyazono, T. M. Skerry, G. R. Mundy, L. F. Bonewal, Dual role for the latent transforming growth factor-beta binding protein in storage of latent TGF-beta in the extracellular matrix and as a structural matrix protein. *J. Cell Biol.* 131 (1995) 539-549.

Dumont, N., C. L. Arteaga, The tumor microenvironment: a potential arbitrator of the tumor suppressive and promoting actions of TGFbeta. *Differentiation.* 70 (2002) 574-582Egeblad, M., Z. Werb, New functions for the matrix metalloproteinases in cancer progression. *Nat Rev. Cancer.* 2 (2002) 161-174.

Fernandez, T., Amoroso, S., Sharpe, S., Jones, G. M., Bliskovski, V., Kovalchuk, A., Wakefield, L. M., Kim, S. J., Potter, M., and Letterio, J. J. (2002) *J. Exp. Med.* 195, 1247-1255.

Gleizes, P. E., R. C. Beavis, R. Mazzieri, B. Shen, D. B. Rifkin, Identification and characterization of an eight-cysteine repeat of the latent transforming growth factor-beta binding protein-1 that mediates bonding to the latent transforming growth factor-beta 1. *J. Biol. Chem.* 271 (1996) 29891-29896.

Glick, A. B., Flanders, K. C., Danielpour, D., Yuspa, S. R., and Sporn, M. B. (1989) *Cell Regul.* 1, 87-97.

Harpel, J., S. Schultz-Cherry, J. E. Murphy-Ullrich, D. B. Rifkin, Tamoxifen and estrogen effects on TGF-b formation: role of thrombospondin-1, avb3, and integrin-associated proteins. *Biochem Biophys Res Commun.* 284 (2001) 11-14.

Hocevar, B. A., and Howe, P. H. (1996) *Proc. Natl. Acad. Sci. USA* 93, 7655-7660.

Hojo, M., T. Morimoto, M. Maluccio, T. Asano, K. Morimoto, M. Lagman, T. Shimbo, M. Suthanthiran, Cyclosporine induces cancer progression by a cell-autonomous mechanism. *Nature.* 397 (1999) 530-534.

Horimoto, M., Kato, J., Takimoto, R., Terui, T., Mogi, Y., and Niitsu, Y. (1995) *British J. Cancer* 72, 676-682.

Kaartinen, V., Voncken, J. W., Shuler, C., Warburton, D., Bu, D., Heisterkamp, N., and Groffen, J. (1995) *Nat. Genet.* 11, 415-421.

Knabbe, C., Zugmaier, G., Schmahl, M., Dietel, M., L-ippman, M. E., and Dickson, R. B., (1991) *Am. J. Clin. Oncol.* 14, S15-20.

Koli, K., and Keski-Oja, J. (1993) *Growth Factors* 8, 153-163.

Koli, K., J. Saharinen, M. Hyytiainen, C. Penttinen, J. Keski-Oja, Latency, activation, and binding proteins of TGF-beta. *Microsc. Res. Tech.* 52 (2001) 354-362.

Kulkarni, A. B., C. G. Huh, D. Becker, A. Geiser, M. Lyght, K. C. Flanders, A. B. Roberts, M. B. Sporn, J. M. Ward, S. Karlsson, Transforming growth factor beta 1 null mutation in mice causes excessive inflammatory response and early death. *Proceedings of the National Academy of Sciences USA.* 90 (1993) 770-774.

Li, J., H. Shen, K. L. Himmel, A. J. Dupuy, D. A. Largaespada, J. D. Nakamura, J. Shaughnessy, N. A. Jenkins, N. G. Copeland, Leukaemia disease genes: large-scale cloning and pathway predictions. *Nat. Gent.* 23 (1999) 348-353.

Li, X., Zhao, X., Fang, Y., Jiang, X., Duong, T., Fan, C., Huang, C. C., and Kain, S. R. (1998) *J. Biol. Chem.* 273, 34970-34975.

Lund, A. H., Turner, G., Trubetskoy, A., Verhoeven, E., Wientjens, E., Hulsman, D., Russell, R., DePinho, R. A., Lenz, J., and van Lohuizen, M. (2002) *Nat. Genet.* 32, 160-165.

Lyons, R. M., Keski-Oja, J., and Moses, H. L. (1988) *J. Cell Biol.* 106, 1659-1665.

Massague, J., Blain, S. W., and La, R. S. (2000) *Cell* 103, 295-309.

Miyazono, K., U. Hellman, C. Wernstedt, C. H. Heldin, Latent high molecular weight complex of transforming growth factor beta 1. Purification from human platelets and structural characterization. *J. Biol. Chem.* 263 (1988) 6407-15.

Miyazono, K., A. Olofsson, P. Colosetti, C. H. Heldin, A role of the latent TGF-b 1-binding protein in the assembly and secretion of TGF-b 1. *EMBO J.* 10 (1991) 1091-1101.

Munger, J. S., J. G. Harpel, F. G. Giancotti, D. B. Rifkin, Interactions between growth factors and integrins: latent forms of transforming growth factor-b are ligands for the integrin avb1. *Mol. Biol. Cell.* 9 (1998) 2627-2638.

Munger, J. S., X. Huang, H. Kawakatsu, M. J. Griffiths, S. L. Dalton, J. Wu, J. F. Pittet, N. Kaminski, C. Garat, M. A. Matthay, D. B. Rifkin, D. Sheppard, The integrin avb6 binds and activates latent TGF-beta 1: a mechanism for regulating pulmonary inflammation and fibrosis. *Cell.* 96 (1999) 319-328.

Munger, J. S., J. G. Harpel, P. E. Gleizes, R. Mazzieri, I. Nunes, D. B. Rifkin, Latent transforming growth factor-beta: structural features and mechanisms of activation. *Kidney Int* 51 (1997) 1376-1382.

Mu, D., S. Cambier, L. Fjellbirkeland, J. L. Baron, J. S. Munger, H. Kawakatsu, D. Sheppard, V. C. Broaddus, S. L. Nishimura, The integrin alpha(v) beta8 mediates epithelial homeostasis through MT1-MMP-dependent activation of TGF-beta1. *J. Cell Biol.* 157 (2002) 493-507.

Murphy-Ullrich, J. E., M. Poczatek, Activation of latent TGF-beta by thrombospondin-1: mechanisms and physiology. *Cytokine Growth Factor Rev.* 11 (2000) 59-69.

Nunes, I., P. E. Gleizes, C. N. Metz, D. B. Rifkin, Latent transforming growth factor-beta binding protein domains involved in activation and transglutaminase-dependent cross-linking of latent transforming growth factor-beta. *J. Cell Biol.* 136 (1997) 1151-1163.

Olofsson, A., K. Miyazono, T. Kanzaki, P. Colosetti, U. Engstrom, C. H. Heldin, Transforming growth factor-b1, -b2, and -b3 secreted by a human glioblastoma cell line. Identification of small and different forms of large latent complexes. *J. Biol. Chem.* 267 (1992) 19482-19488.

Oursler, M. J., Riggs, B. L., and Spelsberg, T. C. (1993) *Endocrinology* 133, 2187-2196.

Onishi, M., S. Kinoshita, Y. Morikawa, A. Shibuya, J. Phillips, L. L. Lanier, D. M. Gorman, G. P. Nolan, A. Miyajima, T. Kitamura, Applications of retrovirus-mediated expression cloning. *Exp. Hematol.* 24 (1996) 324-329.

Proetzel, G., S. A. Pawlowski, M. V. Wiles, M. Yin, G. P. Boivin, P. N. Howles, J. Ding, M. W. Ferguson, T. Doetschman, Transforming growth factor-beta 3 is required for secondary palate fusion. *Nature Genetics.* 11 (1995) 409-414.

Ramirez, F., L. Pereira, The fibrillins. *Int J. Biochem. Cell Biol.* 31 (1999) 255-259.

Rayner, J. R., and Gonda, T. J. (1994) *Mol. Cell. Biol.* 14, 880-887. Kaartinen, V., Voncken, J. W., Shuler, C., Warburton, D., Bu, D., Heisterkamp, N., and Groffen, J. (1995) *Nat. Genet.* 11, 415-421.

Rifkin, D. B., R. Mazzieri, J. S. Munger, I. Noguera, J. Sung, Proteolytic control of growth factor availability. *APMIS.* 107 (1999) 80-85.

Rodriguez, C., Huang, L. J., Son, J. K., McKee, A., Xiao, Z., and Lodish, H. F. (2001) *J. Biol. Chem.* 276, 30224-30230.

Rogers, N. C., Schindler, C., Stark, G. R., Ihle, J. N., and et al. (1993) *Nature* 366, 166-170.

Sanford. L. P. Onnsby, I. Gittenberger-de Groot. A. C. Sariola. H. Friedman. R. Boivin, G. P., Cardell, E. L., and Doetschman, T. (1997) *Development* 124, 2659-2670.

Saharinen, J., J. Taipale, J. Keski-Oja, Association of the small latent transforming growth factor-beta with an eight cysteine repeat of its binding protein LTBP-1. *EMBO J.* 15 (1996) 245-253.

Saharinen, J., J. Keski-Oja, Specific sequence motif of 8-cys repeats of TGF-beta binding proteins, LTBPs, creates a hydrophobic interaction surface for binding of small latent TGF-beta. *Mol. Biol. Cell.* 11 (2000) 2691-2704.

Saharinen, J., M. Hyytiainen, J. Taipale, J. Keski-Oja, Latent transforming growth factor-beta binding proteins (LTBPs) structural extracellular matrix proteins for targeting TGF-beta action. *Cytokine Growth Factor Rev.* 10 (1999) 99-117.

Sambrook, J., D. W. Russell (2001) Molecular cloning a laboratory manual, Cold Spring Harbor, N.Y.

Sanford, L. P., I. Ormsby, A. C. Gittenberger-de Groot, H. Sariola, R. Friedman, G. P. Boivin, E. L. Cardell, T. Doetschman, TGFbeta2 knockout mice have multiple developmental defects that are non-overlapping with other TGF-beta knockout phenotypes. *Development.* 124 (1997) 2659-2670.

Schultz-Cherry, S., H. Chen, D. F. Mosher, T. M. Misenheimer, H. C. Krutzsch, D. D. Roberts, J. E. Murphy-Ullrich, Regulation of transforming growth factor-beta activation by discrete sequences of thrombospondin 1. *J. Biol. Chem.* 270 (1995) 7304-7310.

Schultz-Cherry, S., J. Lawler, J. E. Murphy-Ullrich, The type 1 repeats of thrombospondin 1 activate latent transforming growth factor-b. *J. Biol. Chem.* 269 (1994) 26783-26788.

Schultz-Cherry, S., S. Ribeiro, L. Gentry, J. E. Murphy-Ullrich, Thrombospondin binds and activates the small and large forms of latent transforming growth factor-b in a chemically defined system. *J. Biol. Chem.* 269 (1994) 26775-26782.

Schultz-Cherry, S., and Murphy-Ullrich, J. E. (1993) *J. Cell. Biol.* 122; 923-932.

Shull, M. M., I. Ormsby, A. B. Kier, S. Pawlowski, R. J. Diebold, M. Yin, R. Allen, C. Sidman, G. Proetzel, D. Calvin, T. Doestchman, Targeted disruption of the mouse transforming growth factor-beta 1 gene results in multifocal inflammatory disease. *Nature.* 359 (1992) 693-699.

Sime, P. J., Z. Xing, F. L. Graham, K. G. Csaky, J. Gauldie, Adenovector-mediated gene transfer of active transforming growth factor-beta1 induces prolonged severe fibrosis in rat lung. *J. Clin. Invest.* 100 (1997) 768-776.

Simonsen, H., and Lodish, H. F. (1994) *Trends Pharmacal. Sci.* 15, 437-441

Stark, G. R., and Gudkov, A. V. (1999) *Hum. Mol. Genet.* 8, 1925-1938.

Sun, P., Dong, P., Dai, K., Hannon, G. J., and Beach, D. (1998) *Science* 282, 2270-2272.

Taipale, J., K. Miyazono, C. H. Heldin, J. Keski-Oja, Latent transforming growth factor-beta 1 associates to fibroblast extracellular matrix via latent TGF-beta binding protein. *J. Cell Biol.* 124 (1994) 171-181.

Taipale, J., Saharinen, J., and Keski-Oja, J. (1998) *Adv. Cancer Res.* 75, 87-134.

Urashima, M., A. Ogata, D. Chauhan, M. Hatziyanni, M. B. Vidriales, D. A. Dedera, R. L. Schlossman, K. C. Anderson, Transforming growth factor-beta 1: differential effects on multiple myeloma versus normal B cells. *Blood.* 87 (1996) 1928-1038.

van Zoelen, E. J., van Oostwaard, T. M. and de Laat, S. W. (1986) *J. Biol. Chem.* 261, 5003-5009.

Wang, R. F. Wang, X., Johnston, S. L., Zeng, G., Robbins, P. F., and Rosenberg, S. A. (1998) *Cancer Res.* 58, 3519-3525.

Watling, D., Guschin, D., Muller, M., Silvennoinen, O., Witthuhn, B. A., Quelle, F. W., Harrington, J. J., Sherf, B., Rundlett, S., Jackson, P. D., Perry, R., Cain, S., Leventhal, C., Thornton, M., Ramachandran, R., Whittington, J., Lerner, L., Costanzo, D., McElligott, K., Boozer, S., Mays, R., Smith, E., Veloso, N., Klika, A., Hess, J., Cothren, K., Lo, K: Offenbacher, J., Danzig, J., and Ducar, M. (2001) *Nat. Biotechnol.* 19, 440-445.

Wrana, J. L., L. Attisano, J. Carcamo, A. Zentella, J. Doody, M. Laiho, X. F. Wang, J. Massague, TGF-beta signals through a heteromeric protein kinase receptor complex. *Cell.* 71 (1992) 1003-1014.

Yu, Q., and Stamenkovic, I. (2000) *Genes Dev.* 14, 163-176.

Yehualaeshet, T., R. O'Connor, J. Green-Johnson, S. Mai, R. Silverstein, J. E. Murphy-Ullrich, N. Khalil, Activation of rat alveolar macrophage-derived latent transforming growth factor beta-1 by plasmin requires interaction with thrombospondin-1 and its cell surface receptor, CD36. *Am. J. Patholol.* 155 (1999) 841-851.

Zhong, Z., Wen, Z., and Darnell, J. E., Jr. (1994) *Science* 264, 95-98.

What is claimed is:

1. A method of screening for a protein involved in the extracellular regulation of latent TGF-β activation by:
   transducing a cell line comprising a TGF-β responsive promoter operatively linked to a gene encoding a green fluorescent protein with a retroviral cDNA library and enriching the reporter cell line for green fluorescent protein (GFP) in response to TGF-β signaling, wherein the reporter cell line secretes endogenous latent TGF-β such that, upon acquisition of a latent TGF-β activator, GFP expression is induced, and wherein the TGF-β promoter is 3TP/PAI-I;
   growing individual clones created by the reporter cell line;
   co-culturing each individual clone with a second TGF-β reporter cell line comprising a TGF-β responsive promoter operatively linked to luciferase cDNA that produces luciferase in response to TGF-β, wherein the luciferase production identifies positive clones, and wherein the TGF-β promoter is 3TP/PAI-I; and identifying a protein involved in the extracellular regulation of latent TGF-β that is employed by the positive clones.

2. The method according to claim 1, wherein said transducing step is defined as transducing the reporter cell line with a retroviral cDNA library that contains an insert for an activator of latent TGF-β, wherein the cells expressing the activator is GFP-bright.

3. The method according to claim 1, wherein said transducing step is defined as transducing the reporter cell line with a retroviral cDNA library prepared from mRNA isolated from cells that activate TGF-β.

4. The method according to claim 1, wherein said transducing step is defined as transducing the reporter cell line selected from the group consisting of kidney cells (NRK-49F), human pulmonary adenocarcinoma cells, multiple myeloma cells, gliomablastoma cells, primary cell strains, and cells involved with TGF-β action.

5. The method according to claim 1, wherein said transducing step includes isolating GFP-expressing cells by fluorescence-activated cell sorting (FACS).

6. The method according to claim 1, wherein said identifying step is defined as identifying cells that have acquired the ability to activate latent TGF-β-induced luciferase expression in the absence, but not in the presence of, neutralizing antibodies to TGF-β.

7. The method according to claim 1, wherein said co-culturing step occurs in the presence of TGF-β.

8. The method according to claim 1, wherein said co-culturing step occurs in the absence of a TGF-β inhibitor.

9. The method according to claim 1, wherein said identifying step is defined as retrieval of the retrovirus cDNA insert using a polymerase chain reaction.

* * * * *